US011350845B1

(12) United States Patent
Berdanier

(10) Patent No.: US 11,350,845 B1
(45) Date of Patent: Jun. 7, 2022

(54) PHASE-BASED PASSIVE SOURCE LOCATION IN THREE-DIMENSIONS

(71) Applicant: Government of the United States, as represented by the Secretary of the Air Force, Wright-Patterson AFB, OH (US)

(72) Inventor: Charles A. Berdanier, Dayton, OH (US)

(73) Assignee: United States of America as represented by the Secretary of the Air Force, Wright-Patterson AFB, OH (US)

(*) Notice: Subject to any disclaimer, the term of this patent is extended or adjusted under 35 U.S.C. 154(b) by 780 days.

(21) Appl. No.: 16/279,017

(22) Filed: Feb. 19, 2019

Related U.S. Application Data

(60) Provisional application No. 62/656,020, filed on Apr. 11, 2018.

(51) Int. Cl.
| | |
|---|---|
| *A61B 5/00* | (2006.01) |
| *A61B 5/06* | (2006.01) |
| *G01S 5/06* | (2006.01) |
| *A61B 1/04* | (2006.01) |
| *G01S 5/22* | (2006.01) |
| *G01S 5/02* | (2010.01) |

(52) U.S. Cl.
CPC ............. *A61B 5/061* (2013.01); *A61B 1/041* (2013.01); *G01S 5/0226* (2013.01); *G01S 5/06* (2013.01); *G01S 5/22* (2013.01); *A61B 2562/0204* (2013.01)

(58) Field of Classification Search
CPC ..... G01S 5/22; G01S 5/06; G01S 5/10; A61B 5/061; A61B 1/041
See application file for complete search history.

(56) References Cited

PUBLICATIONS

Li, X., Hong S. and Wu, Z., "Bayesian Compressed Sensing based Dynamic Joint Spectrum Sensing and Primary User Localization for Dynamic Spectrum Access," IEEE Globecom 2011.
Liu, L., Han, Z., Wu, Z. and Qian, L., "Collaborative Compressive Sensing based Dynamic Spectrum Sensing and Mobile Primary User Localization in Cognitive Radio Networks," IEEE Globecom 2011.
Patwari, N., Ash, J., Kyperountas, S., Hero A., R. Moses, R. and N.S Correal, "Locating the Nodes", IEEE Signal Processing Magazine, pp. 54-69, Jul. 2005.
(Continued)

*Primary Examiner* — Rajeev P Siripurapu
(74) *Attorney, Agent, or Firm* — AFMCLO/JAZ; James F. McBride

(57) ABSTRACT

Passive location of an emitter is achieved by sensing a signal propagated from the emitter at multiple sensing locations and determining its phase at each sensing location. A three-dimensional region is searched to find an emitter location for which phase estimates of the signal at the emitter location are in good agreement among the sensing locations. An iterative search from a set of starting points in the region may be performed. The region may be subdivided and each region searched in parallel using multiple processors in parallel. Phase at the sensing locations may be determined locally, using synchronized clocks at the sensing locations, or at a common receiver. In the latter case, signal propagation time from the sensing location to the receiver location is taken into account. The emitter may be a wireless endoscopy capsule, for example.

23 Claims, 4 Drawing Sheets

(56) References Cited

PUBLICATIONS

Maroti, M., Kusy, B., Balogh, G., Volgyesi, P., Nadas, A., Molnar, K., Dora, S., and Ledeczi, A., "Radio Interferometric Geolocation", ACM Sensys 2005, Nov. 2005.

Kulakowski, P., Vales-Alonso, J., Egea-Lopez, E., Ludwin, W. and Garcia-Haro, J., "Angle-of-arrival localization based on antenna arrays for wireless sensor networks", Computers and Electrical Engineering 36, pp. 1181-1186, 2010.

Berdanier, C. and Wu, Z.,"Improved Transmitter Localization through Incorporation of Phase Information", 2012 International Waveform Diversity and Design Conference, Jan. 2012.

Mahan, Robert P., Circular Statistical Methods: Applications in Spatial and Temporal Performance Analysis, United States Army Research Institute for the Behavioral and Social Sciences, Special Report 16, AD-A240 751, Apr. 1991.

Berens, Philipp, CircState: A MATLAB Toolbox for Circular Statistics, Journal of Statistical Software, vol. 31, Issue 10, Sep. 2009.

Berdanier, C. and Wu, Z., "A Novel RF Emitter Localization Method through Phase Information", IEEE Radar Conference (RADARCON) 2013, Apr. 2013.

Blahut, R., "Passive and Baseband Surveillance Systems", in Theory of Remote Image Formation, pp. 456-468, 2004.

Berdanier, C. Wicks, M., Baker, C. and Wu, Z., "Phase Based 2-D Passive Source Localization Using Receiver Networks", IET Journal of Radar, Sonar and Navigation, 2017.

Ash, J. and Moses, R.,"Self-Localization of Sensor Networks", in Handbook on Array Processing and Sensor Networks (eds S. Haykin and K. J. R. Liu), Apr. 2010.

Griffiths, H. and Baker, C., "Passive coherent radar systems—part 1: performance prediction", Special issue of IEEE Proceedings on radar, sonar and navigation on Passive radar, vol. 152, pp. 153-159, Jun. 2005.

Griffiths, H. and Baker, C., "Passive coherent radar systems—part 2: performance prediction", Special issue of IEEE Proceedings on radar, sonar and navigation on Passive radar, vol. 152, pp. 153-159, Jun. 2005.

Gurrieri, L., Willink, T., Petosa, A. and Noghanian, S.,"Characterization of the Angle, Delay and Polarization of Multipath Signals for Indoor Environments", IEEE Transactions on Antennas and Propagation, vol. 56, No. 8, pp. 2710-2719, Aug. 2008.

Huang, X. and Guo, Y.,"Frequency-domain AoA Estimation and Beamforming with Wideband Hybrid Arrays", IEEE Transactions on Wireless Communications, vol. 10, No. 8, pp. 2543-2553, 2011.

Jackson, M., "The geometry of bistatic radar systems", IEE Proc., vol. 133, Part F, pp. 604-612, Dec. 1986.

Li, X., Chakravarthy, V., and Wu, Z., "Joint Spectrum Sensing and Primary User Localization for Cognitive Radio via Compressed Sensing," IEEE Milcom 2010.

Peng, R. and Sichitiu, M.,"Angle of Arrival Localization for Wireless Sensor Networks", 3rd Annual IEEE Communications Society on Sensor and Ad Hoc Communications and Networks, 2006, SECON '06, pp. 374-382, Sep. 2006.

Wadhwa, M., Song, M., Rali, V. and Shetty, S.,"The Impact of Antenna Orientation on Wireless Sensor Network Performance", 2nd IEEE International Conference on Computer Science and Information Technology, pp. 143-147, 2009.

Zimmerman, L., Goetz, A., Fisher, G. and Weigel, R.,"GSM Mobile Phone Localization using Time Difference of Arrival and Angle of Arrival Estimation", 2012—9th International Multi-Conference on Systems, Signals and Devices, Mar. 2012.

Blahut, R., "Passive and Baseband Surveillance Systems", in Theory of Remote Image Formation, pp. 469-480, 2004.

PHASE-BASED PASSIVE SOURCE LOCATION IN THREE-DIMENSIONS

STATEMENT OF GOVERNMENT INTEREST

The invention described herein may be manufactured, used, and licensed by or for the Government of the United States for all governmental purposes without the payment of any royalty.

BACKGROUND

Accurate Passive Source Localization (PSL) of unknown radio frequency (RF) transmitters is a challenging issue. If RF transmitters can be localized with sufficient accuracy, a variety of applications can be significantly enhanced. These applications include cognitive radio (CR), dynamic spectrum access (DSA) networks and passive radar. For CR and DSA network applications, it is highly desirable to not only detect the existence of the primary users (PUs), but also estimate their geographical locations. Knowing the locations of existing PUs can significantly improve the secondary users' co-existence with PUs and minimize interference to the PUs and vice versa. Passive radar systems can use emitters of opportunity in a cooperative or non-cooperative to locate targets. When using emitters of opportunity, accurate knowledge of the transmitter location together with some angular resolution is required. However, many emitters of opportunity are omnidirectional.

PSL relies on characteristics of the transmitted signal, which include amplitude, phase, frequency, and time. Prior approaches include: Time Of Arrival/Time Difference of Arrival (TOA/TDOA) for time-based PSL, Phase Difference Of Arrival (PDOA) for phase-based PSL and Received Signal Strength Indicator (RSSI) for amplitude based PSL. Other approaches include interferometric localization using two emitted tones.

PDOA relies on a known baseline distance and the far field approximation to determine the phase difference normal to a pair of sensors. A disadvantage of the PDOA approaches is that antenna positions constrained to be less than a half wavelength, otherwise an ambiguity in direction is introduced.

A further disadvantage is that the antenna must be in the far enough from the emitter that the wave-fronts can be assumed to be planar.

Accordingly, there exists a need for a passive localization receiver and method that does not require the receivers to be closely space on a wavelength scale and, further, does not require the transmitter to be in the far-field of the receivers.

BRIEF DESCRIPTION OF THE DRAWINGS

The accompanying drawings provide visual representations which will be used to more fully describe various representative embodiments and can be used by those skilled in the art to better understand the representative embodiments disclosed and their inherent advantages. The drawings are not necessarily to scale, emphasis instead being placed upon illustrating the principles of the devices, systems, and methods described herein. In these drawings, like reference numerals may identify corresponding elements.

DETAILED DESCRIPTION

Figure 1:
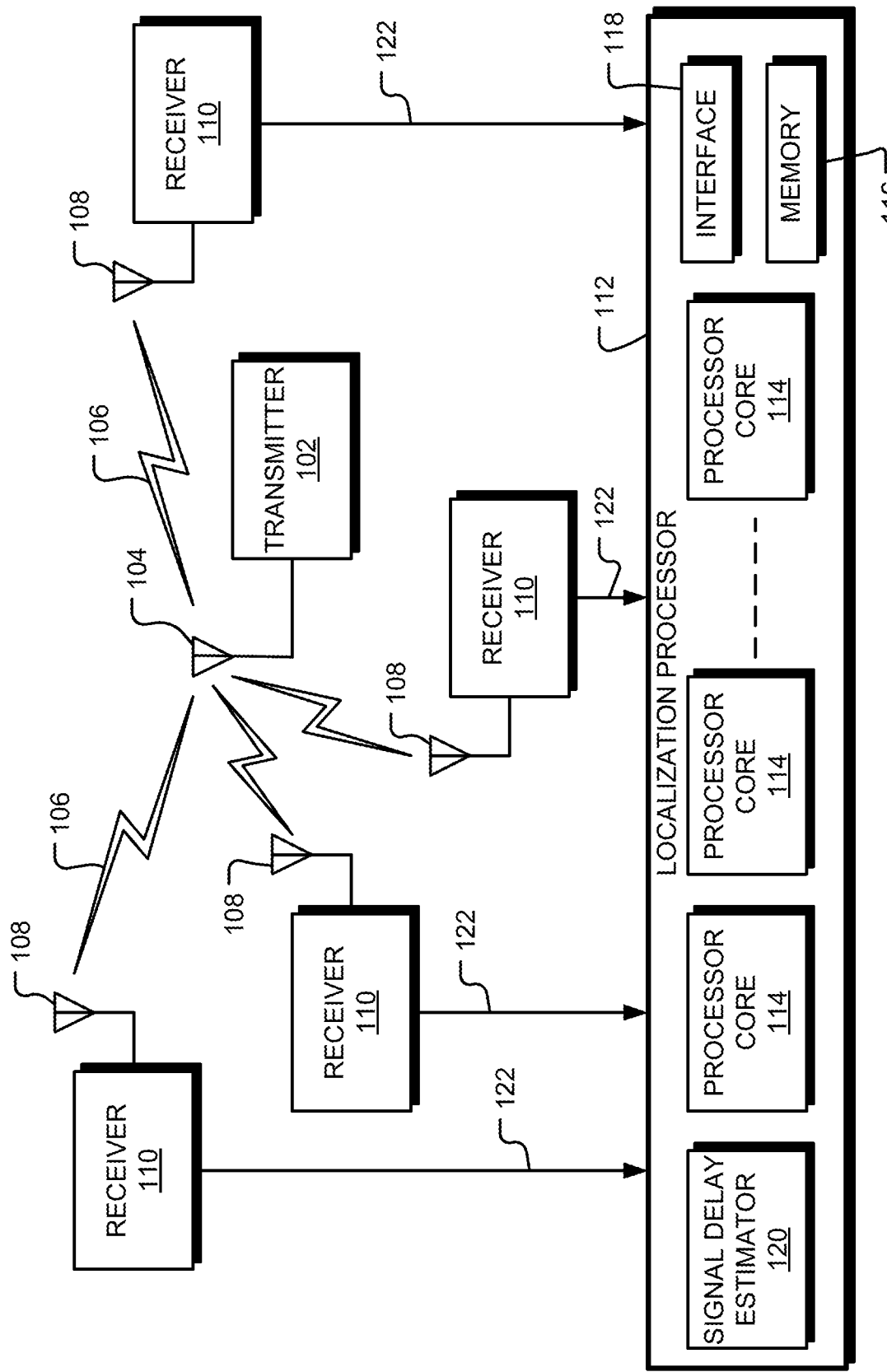
FIG. 1 is a block diagram of a passive source localization (PSL) system, in accordance a representative embodiment.

The various methods, systems, apparatuses, and devices described herein generally provide for the localization of an emitter using a number of passive receivers. Localization is achieved by searching a three-dimensional region to find an emitter location for which phase estimates of the signal at the emitter location, taking into account the receiver locations and the phase at the receiver locations, are in good agreement among the receivers. The search time may be reduced by the use of parallel processing.

While this invention is susceptible of being embodied in many different forms, there is shown in the drawings and will herein be described in detail specific embodiments, with the understanding that the present disclosure is to be considered as an example of the principles of the invention and not intended to limit the invention to the specific embodiments shown and described. In the description below, like reference numerals may be used to describe the same, similar or corresponding parts in the several views of the drawings.

In this document, relational terms such as first and second, top and bottom, and the like may be used solely to distinguish one entity or action from another entity or action without necessarily requiring or implying any actual such relationship or order between such entities or actions. The terms "comprises," "comprising," "includes," "including," "has," "having," or any other variations thereof, are intended to cover a non-exclusive inclusion, such that a process, method, article, or apparatus that comprises a list of elements does not include only those elements but may include other elements not expressly listed or inherent to such process, method, article, or apparatus. An element preceded by "comprises . . . a" does not, without more constraints, preclude the existence of additional identical elements in the process, method, article, or apparatus that comprises the element.

Reference throughout this document to "one embodiment," "certain embodiments," "an embodiment," "implementation(s)," "aspect(s)," or similar terms means that a particular feature, structure, or characteristic described in connection with the embodiment is included in at least one embodiment of the present invention. Thus, the appearances of such phrases or in various places throughout this specification are not necessarily all referring to the same embodiment. Furthermore, the particular features, structures, or characteristics may be combined in any suitable manner in one or more embodiments without limitation.

The term "or" as used herein is to be interpreted as an inclusive or meaning any one or any combination. Therefore, "A, B or C" means "any of the following: A; B; C; A and B; A and C; B and C; A, B and C." An exception to this definition will occur only when a combination of elements, functions, steps or acts are in some way inherently mutually exclusive. Also, grammatical conjunctions are intended to express any and all disjunctive and conjunctive combinations of conjoined clauses, sentences, words, and the like, unless otherwise stated or clear from the context. Thus, the term "or" should generally be understood to mean "and/or" and so forth.

All documents mentioned herein are hereby incorporated by reference in their entirety. References to items in the singular should be understood to include items in the plural, and vice versa, unless explicitly stated otherwise or clear from the text.

Recitation of ranges of values herein are not intended to be limiting, referring instead individually to any and all values falling within the range, unless otherwise indicated, and each separate value within such a range is incorporated into the specification as if it were individually recited herein. The words "about," "approximately," or the like, when accompanying a numerical value, are to be construed as indicating a deviation as would be appreciated by one of ordinary skill in the art to operate satisfactorily for an intended purpose. Ranges of values and/or numeric values are provided herein as examples only, and do not constitute a limitation on the scope of the described embodiments. The use of any and all examples, or exemplary language ("e.g.," "such as," or the like) provided herein, is intended merely to better illuminate the embodiments and does not pose a limitation on the scope of the embodiments. No language in the specification should be construed as indicating any unclaimed element as essential to the practice of the embodiments.

For simplicity and clarity of illustration, reference numerals may be repeated among the figures to indicate corresponding or analogous elements. Numerous details are set forth to provide an understanding of the embodiments described herein. The embodiments may be practiced without these details. In other instances, well-known methods, procedures, and components have not been described in detail to avoid obscuring the embodiments described. The description is not to be considered as limited to the scope of the embodiments described herein.

In the following description, it is understood that terms such as "first," "second," "top," "bottom," "up," "down," "above," "below," and the like, are words of convenience and are not to be construed as limiting terms. Also, the terms apparatus and device may be used interchangeably in this text.

Passive source localization uses a number of sensors (such as antenna, microphones, hydrophones, photodetectors, etc.) to sense a signal emitted from a source and, from the sensor signals, estimate the location of the source. Various properties of the source, such as frequency, amplitude and phase, may be determined from the sensor signals.

In general, the devices, systems, and methods described herein may implement a passive source localization (PSL) technique that is based on estimating the phase of a number of sensor signals and then performing a search of a selected volume to find a source location for which the source phase, predicted from the observed phase, is in good agreement between the receivers.

A similar approach has been used for source localization in two-dimensions, however, the approach is computationally intensive and, as disclosed, not suitable for practical applications.

The search volume may be selected in various ways. For example, when using omnidirectional receivers, methods such as Received Signal Strength (RSSI) can be used to limit the search volume.

Unlike the phase-difference-of-arrival (PDOA) approach, the disclosed technique does not depend on relative sensor locations or the far field approximation.

FIG. 1 is a block diagram of a passive source localization (PSL) system 100 in accordance with certain embodiments of the disclosure. An emission source, shown here as transmitter 102 and antenna 104, emits propagating signals 106 that are sensed by sensors of the PSL system. The sensors are shown here as antenna 108 and receivers 110, but other types of sensors may be used depending upon the nature of the emitted signal 106. Signals from the sensors are passed to localization processor 112.

In accordance with a first aspect of the disclosure, localization processor 112 includes two or more processing cores 114. These processing cores are configured to perform computations for source localization in parallel. The use of multiple processing cores operating in parallel reduces the time taken to process the sensor signals and estimate the source location. Parallel processors are known in the art for use in applications such as graphics processing. Such processors are in widespread use and, consequently, are relatively inexpensive.

Localization processor 112 includes a memory 116 for data and program instructions. At least some the memory may be accessible by multiple processing cores to enable sharing of data between the processing cores. Localization processor 112 also includes interface 118, such as a user interface or network interface that may be used for control of the processor and data input and output.

In the embodiment shown, localization processor 112 includes signal delay estimator 120. Since the sensors (antenna 108 in this example) are distributed in space, the signals are passed to the location processor on signal links 122. These may be wired, optical or wireless links for example. It takes a finite amount of time for signals to traverse the links. In some applications, such as estimating the source of a radio frequency (RF) source, the delays are large enough compared with the period of the signals to introduce a significant phase shift. In such situations, the signal delays must be estimated and compensated for. In one embodiment, for example, a time-delay reflectometer is used to measure the delays. In other applications, such as acoustic localization, the delays are small and may be neglected.

Figure 2:
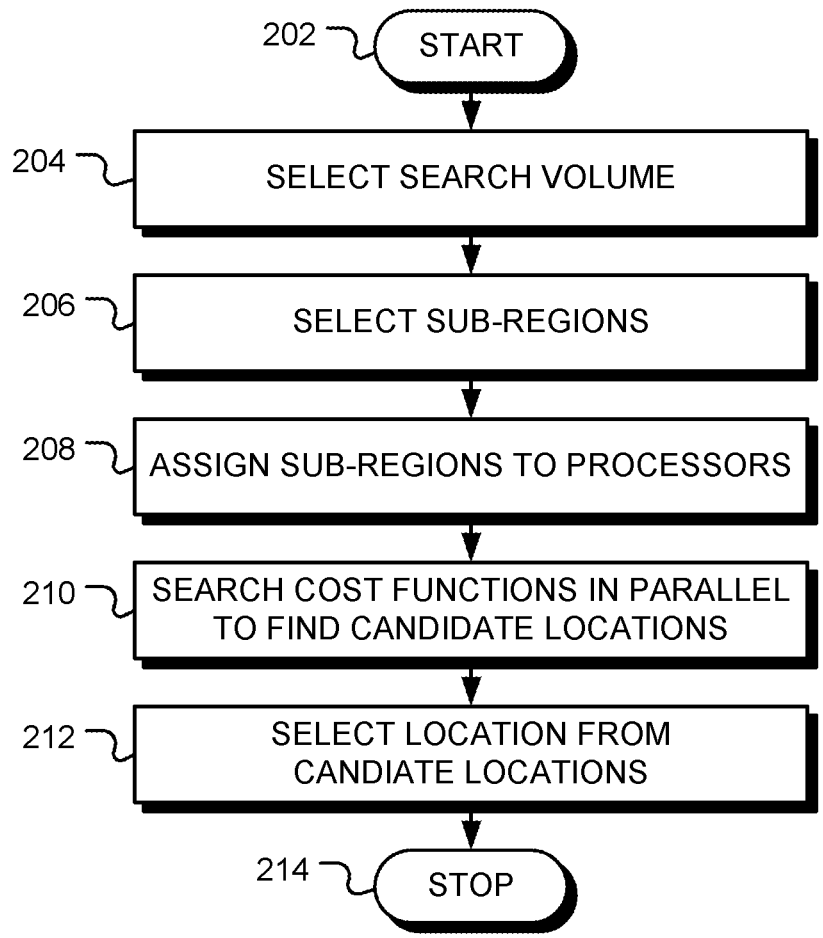
FIG. 2 is a flow chart of a method for passive source location, in accordance a representative embodiment.

FIG. 2 is a flow chart of a method 200 for passive source location in accordance with the disclosure. Following start block 202, a search volume is selected at block 204. The search volume may be selected in various ways. For example, a prior approximate source location may be known, or the approximate source location may be determined by other, less accurate, techniques such as RSSI. The search volume is partitioned into a number of sub-regions at block 206. At block 208, the sub-regions are assigned to processing cores. Each processor core is assigned a sub-set of the sub-regions. At block 210, the processing cores search the sub-regions in parallel to find candidate source locations for which the source phase is in good agreement when predicted from all of the sensors. This may be done by minimizing a cost function (or, equivalently, maximizing a benefit function). At block 212, the final estimate of the source location is selected from the candidate source locations. The method terminates at block 214.

Figure 3:
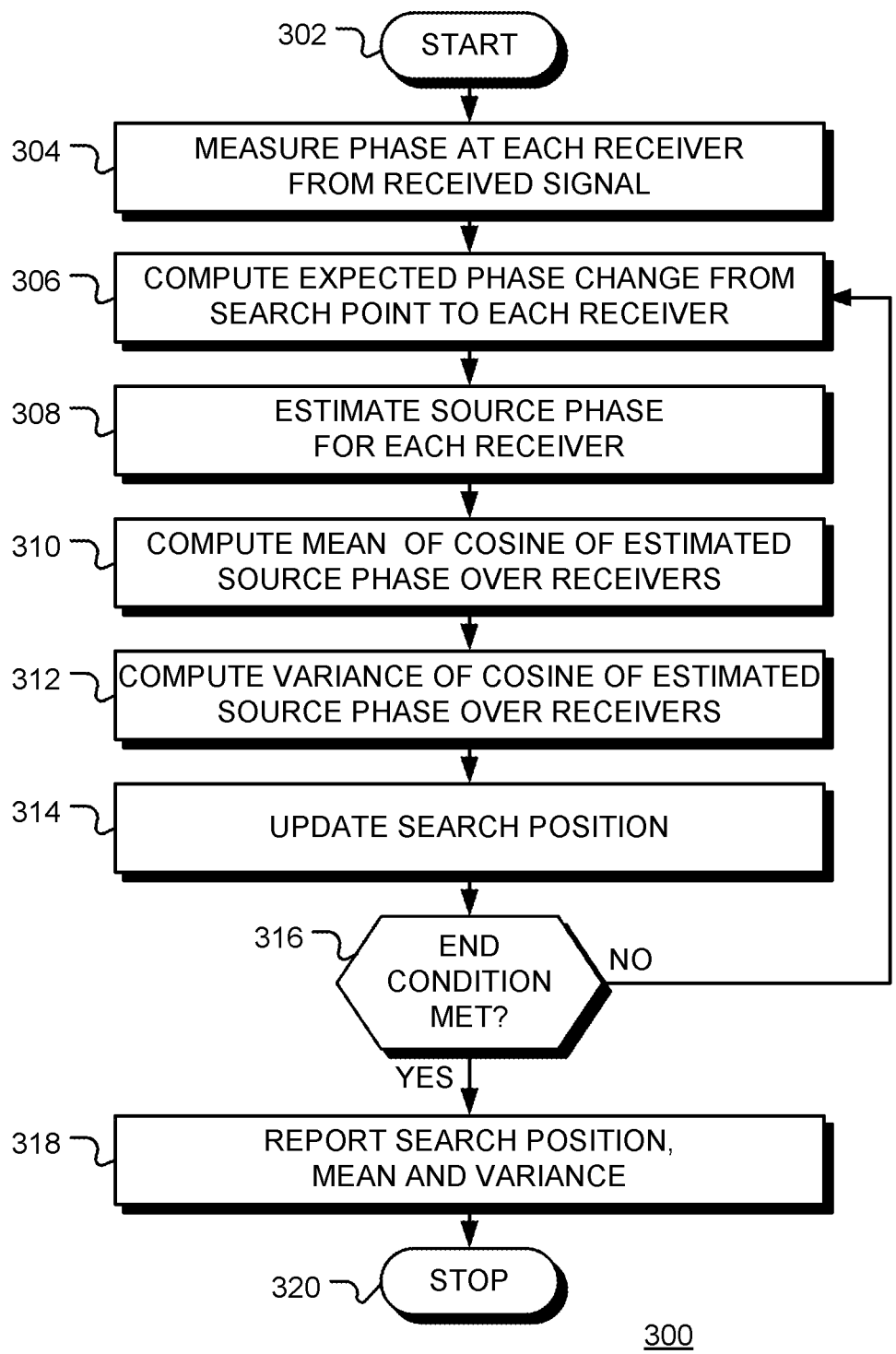
FIG. 3 is a further flow chart of a method of passive source localization, in accordance with a representative embodiment.

FIG. 3 is a further flow chart of a method 300 of passive source localization in accordance with embodiments of the disclosure. FIG. 3 describes a method of searching a sub-region. Following start block 302, the phase of the emitted signal is estimated at each of the receivers at block 304. At block 306, the expected phase change from a search point to the receiver is computed. This uses knowledge of the location of the receiver and the wavelength of the propagated signal. The wavelength can, in turn, be computed from the frequency of the signal and its speed of propagation. The phase of the emitted signal at the source location (which is assumed to be a point source) is then computed at block 308 for each receiver. As discussed above, any propagation delay in the signal links is compensated for in this calculation. At blocks 310 and 312, a measure of the degree of agreement between the source phase estimates at the receiver is determined and used, at block 314 to update the search position. In FIG. 3, a mean value of the complex phasors of the angles is computed at block 310 and the variance is computed at block 312. However, other measures of the degree of agreement may be used. Updating the search position may be done by using a gradient algorithm, by searching over a grid or some other method. When an end condition is met, as depicted by the positive branch from decision block 316, the found position is output at block 318, together with a measure of the agreement. Example end conditions include a level of agreement above some threshold or a designated number of positions searched. The method terminates at block 320. If the end condition is not met, as depicted by the negative branch from decision block 316, flow returns to block 306.

In one embodiment, the cost function is variance of the cosine of the estimated source phase. For this embodiment, the mean of the cosine of the estimated source phase is computed at block 310 and the variance about the mean is computed at block 312. An alternative metric is described in detail below.

The disclosed approach computes the phase at each receiver from an assumed transmitter location. In contrast, prior approaches, such as the phase difference of arrival (PDOA) approach computes the transmitter location from measured phase differences at the receivers. In addition, the PDOA is restricted to applications where the receivers are in the far-field of the transmitters. This restriction does not apply to the disclosed localization technique. Still further, the PDOA approach restricts the receivers to be less than one half-wavelength apart. This restriction does not apply to the disclosed localization technique, rather the disclosed approach may benefit from spaced receivers.

Figure 4:
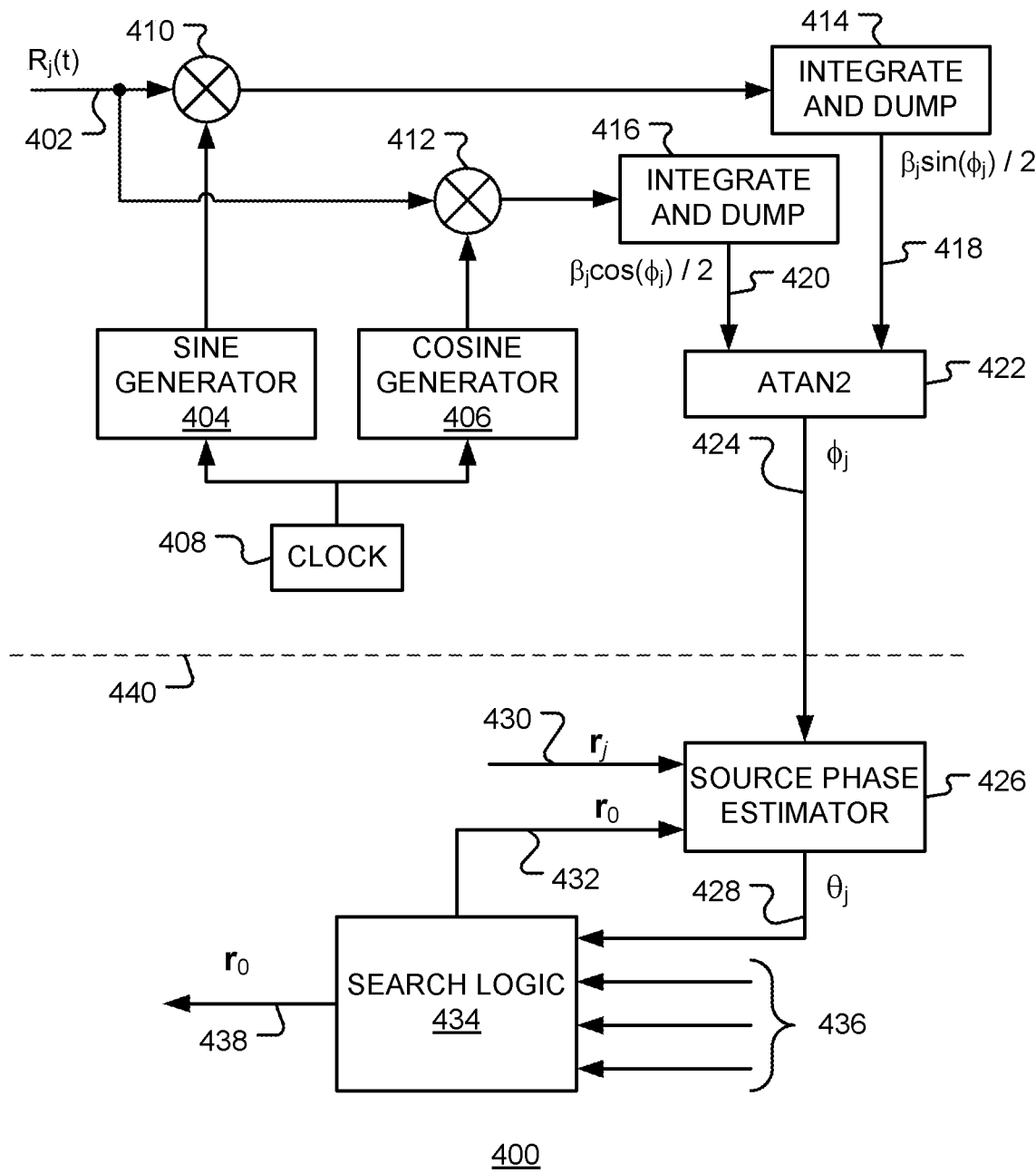
FIG. 4 is a block diagram of a localization processor, in accordance with a representative embodiment.

FIG. 4 is a block diagram of a localization processor 400 in accordance with an embodiment of the disclosure. The signal at a transmitter is denoted as $$T(t) = \alpha \cos(\omega t + \theta) \tag{1}$$

where $\alpha$ is the amplitude, $\omega = 2\pi \cdot f$ is the radian frequency and $\theta$ is a phase offset in radians. Referring to FIG. 4, the response 402 at receiver j is $$R_j(t) = \beta \cos(\omega t + \phi_j) + \Sigma S_{MP}(t) + \Sigma S_C(t) + \eta_0(t) \tag{2}$$

where $\Sigma S_{MP}(t)$ is a component of the signal due to multipath, $\Sigma S_C(t)$ is a component due to other signals and $\eta_0(t)$ is a noise component. Sine generator 404 and cosine generator 406 are driven by clock 408 to provide in-phase and quadrature demodulation signals. The demodulation signals are applied in multipliers 410 and 412. The results are integrated over a number of cycles and dumped in elements 414 and 416. The sine (418) and cosine (420) components of the demodulated signal can be compactly represented as the imaginary and real parts, respectively of a complex signal. The complex demodulated signal (after compensating for signal delays) at receiver j is $$s_j = \frac{1}{T} \int_0^T e^{-i\omega t} R_j(t) dt \tag{3}$$

$$= \frac{1}{T} \int_0^T e^{-i\omega t} \left\{ \frac{\beta}{2} \left[ e^{i(\omega t + \phi_j)} + e^{-i(\omega t + \phi_j)} \right] + \sum S_{MP}(t) + \sum S_C(t) + \eta_0(t) \right\} dt$$

$$= \frac{\hat{\beta}_j}{2} e^{i\hat{\phi}_j}$$

where T is a whole number of cycles of the signal, $\hat{\beta}_j$ is the estimated amplitude of the direct signal and $\hat{\phi}_j$ is the estimated phase. The term $e^{i\hat{\phi}_j}$ is a complex phasor of the estimated phase angle $\hat{\phi}_j$. The estimated phase 424 at sensing location j is computed in arctangent unit 422 as $$\hat{\phi}_j = \operatorname{atan2}\left\{ -\int_0^T \sin(\omega t) R_j(t) dt, \int_0^T \cos(\omega t) R_j(t) dt \right\}, \tag{4}$$

where T is a whole number of cycles of the signal and 'a tan 2' denotes the four-quadrant inverse tangent function.

The operations may be performed in the continuous time domain, as described above, or in a discrete time domain, or in a combination thereof. In the discrete time domain, the signals are sampled at times $t = nT_s$, where n is an integer and $T_s$ is a sampling interval. The sampling interval may be selected such that the sampling frequency is at least twice the highest frequency present in the signal. In the discrete time version, the integrals in equation (4) are replaced by summations.

The estimated phase of the signal at vector sensing location $r_j$ is related to the phase of the signal $\theta$ at vector source location $r_0$ by $$\hat{\phi}_j = \theta - k|r_j - r_0| + \varepsilon_j \tag{5}$$

where $$k = \frac{2\pi}{\lambda}$$

is the wavenumber of the propagated signal, $\lambda$ is the wavelength and $\varepsilon_j$ is an error term due to the presence of multipath signals and other interference.

When the emitter is at estimated position vector $\hat{r}_0$, the estimated phase at the emitter is $$\hat{\theta}_j(\hat{r}_0) = \hat{\phi}_j + k|r_j - \hat{r}_0|. \tag{6}$$

This computation is performed in source phase estimator 426 in FIG. 4. As indicated in the figure, the estimated source phase is dependent upon the sensing location $r_j$ (430) and the source location $\hat{r}_0$. In addition, the estimated source phase is dependent upon the wavenumber k. The source localization problem is to estimate a position vector $\hat{r}_0$ for which the estimates $\hat{\theta}_j$ of the source phase are in the closest agreement among all of the receivers. This is done by searching a three-dimensional space for a location the closest agreement among all of the receivers. The search is performed by search logic 434. In addition to receiving the estimate source phase for sensing location j, search logic receives estimated source phases 436 from other sensing locations. From this information, a revised or updated search location 432 ($\hat{r}_0$) is determined and provided to the source phase estimator for the next iteration of the search. At the end of the search, the estimated source location is output as vector 438.

Search logic 434 relies upon a metric to quantify the degree of agreement between the source phases estimated at the different receives. An example metric, which corresponds to distance metric between phasors in the complex plane, is described below. However, it will be apparent to those of skill in the art that other metrics may be used without departing from the present disclosure.

In FIG. 4, the elements above broken line 440 form a phase detector. The phase detector may be implemented at each of the sensing locations, in which case clocks 408 at each location should be synchronized or at least have a known relationship. Alternatively, the phase detectors may be implemented at the receiver location. In that embodiment, the signals 402 are transmitted to the receiver location and the time taken for the transmission should be compensated for. This may be done, for example, using a time domain reflectometer, for example, to estimate delays in a wired link or by measuring or computing time of flight for a wireless link.

In an example embodiment, the disclosed system and method may be used to locate an emitter located in a wireless endoscopy capsule or other internal sensor in a living body. For example, the sensors are arranged on a support structure configured to be placed in contact with, or in close proximity to, a living body. The structure may be a curved plate shaped to be placed against the body of a person having swallowed a wireless endoscopy capsule. The wireless endoscopy capsule emits a signal of a known frequency, such as 403.5 MHz, for example. Such a system enables the location of the capsule, relative the support structure, to be determined. The position of the support structure relative to the body may be determined by direct measurement to particular body features.

Example Metric

The phasor $e^{i\hat{\phi}_j}$ in equation (3) defines a position in the complex plane. The mean position, in the complex plane, of the phasors for each of the N receivers is computed as $$\mu(\hat{r}_o) = \frac{1}{N}\sum_{j=1}^{N} e^{i\theta_j(\hat{r}_o)} \quad (7)$$

The mean square distance, in the complex plane, to the mean position is given by the variance $$\sigma^2(\hat{r}_o) = \frac{1}{N}\sum_{j=1}^{N}\left|e^{i\theta_j(\hat{r}_o)} - \mu(\hat{r}_o)\right|^2 \quad (8)$$

This can be simplified as $$\sigma^2(\hat{r}_o) = \frac{1}{N}\sum_{j=1}^{N}\left(e^{i\theta_j} - \mu\right)\left(\overline{e^{i\theta_j} - \mu}\right) \quad (9)$$

$$= \frac{1}{N}\sum_{j=1}^{N}\left(1 - \overline{\mu}e^{i\theta_j} - \mu e^{i\theta_j} + |\mu|^2\right)$$

$$= 1 - |\mu(\hat{r}_o)|^2$$

where the superposed bar denotes the complex conjugate.

Thus, the variance is simply related to the mean and no explicit computation is required. Accordingly, the variance $\sigma^2(\hat{r}_o)$ may be minimize by maximizing the absolute value $|\mu(\hat{r}_o)|$ of the complex mean. Note that the mean is always within the unit circle, so the variance is always positive.

The localization method begins by estimating the phase 424 at each sensing location j as $$\hat{\phi}_j = atan2\left\{-\int_0^T \sin(\omega t)R_j(t)dt, \int_0^T \cos(\omega t)R_j(t)dt\right\}, \quad (10)$$

where T is a whole number of cycles of the signal and 'a tan 2' denotes the four-quadrant inverse tangent function. This operation may be performed in the continuous or discrete time domains. For each sensing location and each search position $\hat{r}_0$, the unit 426 computes the estimated emitter phase as $$\hat{\theta}_j(\hat{r}_0) = \hat{\phi}_j + k|r_j - \hat{r}_0|. \quad (11)$$

The cosine and sine components of the complex phasor of $\hat{\theta}_j(\hat{r}_0)$ are summed to give $$S_c(\hat{r}_0) = N\mu_{real} = \sum_{j=1}^{N}\cos(\hat{\theta}_j(\hat{r}_0)), \quad (12)$$

$$S_s(\hat{r}_0) = N\mu_{imag} = \sum_{j=i}^{N}\sin(\hat{\theta}_j(\hat{r}_0)).$$

The metric is then computed as $$J(\hat{r}_0) = N^2|\mu|^2 = S_c^2(\hat{r}_0) + S_s^2(\hat{r}_0). \quad (13)$$

The metric is largest (closest to unit absolute value) when all estimates are clustered together.

The purpose of the search is to discover locations for which there is good agreement between the phase estimates at the receivers. It will be apparent to those of ordinary skill in the art that other metrics may be used. For example, the circular covariance, defined as $1-|\mu(\hat{r}_o)|$, may be minimized.

The above systems, devices, methods, processes, and the like may be realized in hardware, software, or any combination of these suitable for a particular application. The hardware may include a general-purpose computer and/or dedicated computing device. This includes realization in one or more microprocessors, microcontrollers, embedded microcontrollers, programmable digital signal processors or other programmable devices or processing circuitry, along with internal and/or external memory. This may also, or instead, include one or more application specific integrated circuits, programmable gate arrays, programmable array logic components, or any other device or devices that may be configured to process electronic signals. It will further be appreciated that a realization of the processes or devices described above may include computer-executable code created using a structured programming language such as C, an object oriented programming language such as C++, or any other high-level or low-level programming language (including assembly languages, hardware description languages, and database programming languages and technologies) that may be stored, compiled, or executed to run on one of the above devices, as well as heterogeneous combinations of processors, processor architectures, or combinations of different hardware and software. In another implementation, the methods may be embodied in systems that perform the steps thereof, and may be distributed across devices in a number of ways. At the same time, processing may be distributed across devices such as the various systems described above, or all of the functionality may be integrated into a dedicated, standalone device or other hardware. In another implementation, means for performing the steps associated with the processes described above may include any of the hardware and/or software described above. All such permutations and combinations are intended to fall within the scope of the present disclosure.

Application programming interfaces (APIs) and programming models, such as the CUDA® API of NVIDIA Corporation, may be used to provide access to a virtual instruction set and parallel computational elements of a graphic processing unit. The use of parallel processing in graphics processing unit enables many sub-regions to be searched in parallel, thereby greatly reducing computation time for localization.

Embodiments disclosed herein may include computer program products comprising computer-executable code or computer-usable code that, when executing on one or more computing devices, performs any and/or all of the steps thereof. The code may be stored in a non-transitory fashion in a computer memory, which may be a memory from which the program executes (such as random-access memory associated with a processor), or a storage device such as a disk drive, flash memory or any other optical, electromagnetic, magnetic, infrared or other device or combination of devices. In another implementation, any of the systems and methods described above may be embodied in any suitable transmission or propagation medium carrying computer-executable code and/or any inputs or outputs from same.

It will be appreciated that the devices, systems, and methods described above are set forth by way of example and not of limitation. Absent an explicit indication to the contrary, the disclosed steps may be modified, supplemented, omitted, and/or re-ordered without departing from the scope of this disclosure. Numerous variations, additions, omissions, and other modifications will be apparent to one of ordinary skill in the art. In addition, the order or presentation of method steps in the description and drawings above is not intended to require this order of performing the recited steps unless a particular order is expressly required or otherwise clear from the context.

The method steps of the implementations described herein are intended to include any suitable method of causing such method steps to be performed, consistent with the patentability of the following claims, unless a different meaning is expressly provided or otherwise clear from the context. So, for example performing the step of X includes any suitable method for causing another party such as a remote user, a remote processing resource (e.g., a server or cloud computer) or a machine to perform the step of X. Similarly, performing steps X, Y, and Z may include any method of directing or controlling any combination of such other individuals or resources to perform steps X, Y, and Z to obtain the benefit of such steps. Thus, method steps of the implementations described herein are intended to include any suitable method of causing one or more other parties or entities to perform the steps, consistent with the patentability of the following claims, unless a different meaning is expressly provided or otherwise clear from the context. Such parties or entities need not be under the direction or control of any other party or entity, and need not be located within a particular jurisdiction.

It should further be appreciated that the methods above are provided by way of example. Absent an explicit indication to the contrary, the disclosed steps may be modified, supplemented, omitted, and/or re-ordered without departing from the scope of this disclosure.

It will be appreciated that the methods and systems described above are set forth by way of example and not of limitation. Numerous variations, additions, omissions, and other modifications will be apparent to one of ordinary skill in the art. In addition, the order or presentation of method steps in the description and drawings above is not intended to require this order of performing the recited steps unless a particular order is expressly required or otherwise clear from the context. Thus, while particular embodiments have been shown and described, it will be apparent to those skilled in the art that various changes and modifications in form and details may be made therein without departing from the scope of this disclosure and are intended to form a part of the disclosure as defined by the following claims, which are to be interpreted in the broadest sense allowable by law.

The various representative embodiments, which have been described in detail herein, have been presented by way of example and not by way of limitation. It will be understood by those skilled in the art that various changes may be made in the form and details of the described embodiments resulting in equivalent embodiments that remain within the scope of the appended claims.

The invention claimed is:

1. A method for locating an emitter comprising:
sensing a signal propagated from the emitter at a plurality of sensing locations;
determining a phase of the propagated signal at each of the plurality of sensing locations;
determining a three-dimensional search region that includes the emitter location;
for each of a plurality of sub-regions within the three-dimensional search region:
determining an estimated emitter phase for each sensing location dependent upon the phase of a signal at each of the plurality of sensing locations and a distance between a location in the sub-region and the sensing location; and
evaluating a cost function to determine a degree of agreement between the estimated emitter phases at the plurality of sensing locations;
determining one or more initial emitter locations for which the degree of agreement between the estimated emitter phases at the plurality of sensing locations is above a threshold value; and
selecting a final location of the emitter from the one or more initial emitter locations.

2. The method of claim 1, where determining the phase of the signal at a sensing location of the plurality of sensing locations comprises:
transmitting the sensed signal at the sensing location to a receiver;
compensating for a time delay associated with the transmission of the signal; and
demodulating the signal.

3. The method of claim 2, further comprising measuring the time delay in transmitting the sensed signal to the receiver using time domain reflectometry.

4. The method of claim 1, further comprising, for each of the plurality of sub-regions:

searching the sub-region to determine a location within the sub-region for which the agreement between the estimated emitter phases at the plurality of sensing locations is maximized.

5. The method of claim 4, where the searching is performed using a conjugate-gradient technique.

6. The method of claim 1, where the three-dimensional search region is determined from received signal strengths of the propagated signal at the plurality of sensing locations.

7. The method of claim 1, further comprising:
dividing the plurality of sub-regions into N sets of sub-regions, where N is greater than one;
allocating each of the N sets of sub-regions to a processing unit of N processing units; and
for each processing unit of the N processing units in parallel:
determining the location of the emitter in the corresponding set of sub-regions for which the degree of agreement between the estimated emitter phases at the plurality of sensing locations is maximized;
where determining the location of the emitter comprises comparing cost functions for the determined locations in the N sets of sub-regions.

8. The method of claim 1, where selecting the final location of the emitter from the one or more initial emitter locations comprises selecting the initial location for which the degree of agreement between the estimated emitter phases at the plurality of sensing locations is maximized.

9. The method of claim 1, where selecting the final location of the emitter from the one or more initial emitter locations comprises forming a weighted sum of the initial location.

10. The method of claim 9, where each initial location is weighted in accordance with the degree of agreements between the estimated emitter phases for that initial location.

11. The method of claim 1, further comprising:
selecting a size of each sub-region of the plurality of sub-regions such that a maximum dimension of the sub-region is less than one wavelength of the propagating signal.

12. The method of claim 1, where the cost function is a differentiable function of the emitter location.

13. A method for locating an emitter comprising:
sensing a signal propagated from the emitter at a plurality of sensing locations;
determining, at a receiver, a phase of the propagated signal at each of the plurality of sensing locations;
in the receiver:
determining a three-dimensional search region that includes the emitter location;
for each of one or more sub-regions within the three-dimensional search region:
determining an estimated emitter phase for each sensing location dependent upon the phase of propagated signal at each of the plurality of sensing locations and a distance between a location in the sub-region and the sensing location; and
evaluating a cost function to determine a degree of agreement between the estimated emitter phases at the plurality of sensing locations;
determining one or more initial emitter locations for which the degree of agreement between the estimated emitter phases at the plurality of sensing locations is above a threshold value; and
selecting a final location of the emitter from the one or more initial emitter locations.

14. The method of claim 13, where determining, at the receiver, the phase of the signal at a sensing location of the plurality of sensing locations comprises:
transmitting the sensed signal at the sensing location to the receiver;
compensating for a time delay associated with the transmission of the signal; and
demodulating the signal.

15. The method of claim 13, where determining, at the receiver, the phase of the signal at the plurality of sensing locations comprises:
synchronizing, in time, phase detectors at each of the plurality of sensing locations;
detecting, by the phase detectors, the phase at each of the plurality of sensing locations; and
transmitting the detected phases to the receiver.

16. An apparatus for locating an emitter, comprising:
a plurality of sensors configured to sense a signal propagated from the emitter at a plurality of sensing locations to provide a plurality of sensed signals;
a receiver;
a plurality of connections that couple the plurality of sensed signals to the receiver;
where the receiver comprises:
a demodulator configured to determine phases of the propagating signal from the plurality of sensed signals; and
one or more processors configured to:
for each of a plurality of sub-regions in a three-dimensional search region:
determine an estimated emitter phase for each sensing location dependent upon the phase of the propagating signal at each of the plurality of sensing locations and a distance between a location in the sub-region and the sensing location; and
evaluate a cost function to determine a degree of agreement between the estimated emitter phases at the plurality of sensing locations;
determine one or more initial emitter locations for which the degree of agreement between the estimated emitter phases at the plurality of sensing locations is above a threshold value; and
select a final location of the emitter from the one or more initial emitter locations.

17. The apparatus of claim 16, where the propagating signal comprises a radio signal and the plurality of sensors comprise antenna.

18. The apparatus of claim 16, where the propagating signal comprises an acoustic signal and the plurality of sensors comprise acoustic transducers.

19. The apparatus of claim 16, further comprising a time domain reflectometer configured to measure time delays associated with transmitting a sensed signal along each of the plurality of connections, where the demodulator is further configured to compensate for the measured time delays in determining the phases of the propagating signal at the sensing locations.

20. The apparatus of claim 16, where the one or more processors comprise N processors, where N is greater than one and where computations for the plurality sub-regions are performed by the N processors in parallel.

21. The apparatus of claim 16, where the one or more processors comprise one or more graphics processors.

22. The apparatus of claim 16, where the emitter is located in a wireless endoscopy capsule.

23. The apparatus of claim 16, where the plurality of sensors are arranged to enable placement in contact with, or in close proximity to, a living body.

\* \* \* \* \*